(12) United States Patent
Dornhof

(10) Patent No.: US 12,357,367 B2
(45) Date of Patent: Jul. 15, 2025

(54) GENERATOR FOR SUPPLYING MEDICAL INSTRUMENTS

(71) Applicant: Erbe Elektromedizin GmbH, Tuebingen (DE)

(72) Inventor: Konstantin Dornhof, Horb am Neckar (DE)

(73) Assignee: ERBE ELEKTROMEDIZIN GMBH, Tuebingen (DE)

( * ) Notice: Subject to any disclaimer, the term of this patent is extended or adjusted under 35 U.S.C. 154(b) by 137 days.

(21) Appl. No.: 18/067,149

(22) Filed: Dec. 16, 2022

(65) Prior Publication Data

US 2023/0198389 A1 Jun. 22, 2023

(30) Foreign Application Priority Data

Dec. 22, 2021 (EP) ..................... 21217016

(51) Int. Cl.
*H02M 7/538* (2007.01)
*A61B 18/12* (2006.01)

(52) U.S. Cl.
CPC ......... *A61B 18/1206* (2013.01); *H02M 7/538* (2013.01)

(58) Field of Classification Search
CPC .......................... A61B 18/1206; H02M 7/538
See application file for complete search history.

(56) References Cited

U.S. PATENT DOCUMENTS

| 5,559,684 A | * | 9/1996 | Ohms | ................. | H02M 3/3374 363/101 |
| 2003/0163124 A1 | | 8/2003 | Goble | | |
| 2015/0280452 A1 | * | 10/2015 | Nalbant | ................. | H02J 50/12 307/104 |

(Continued)

FOREIGN PATENT DOCUMENTS

| DE | 2910196 B1 | 9/1980 |
| DE | 602004009293 T2 | 7/2008 |

(Continued)

OTHER PUBLICATIONS

International European Search Report for European Application No. 21217016.1-1126 dated Jun. 15, 2022; 11 pages.

*Primary Examiner* — Harry R Behm
(74) *Attorney, Agent, or Firm* — Fitch, Even, Tabin & Flannery LLP

(57) ABSTRACT

A push-pull generator provided for supply of a medical instrument includes at least one capacitive branch connected to ground, preferably in a switchable configuration, in parallel to at least one of its two transistors. Such a capacitive switchable branch can consist of a series connection of one capacitor and one switch. Thereby one of the two half waves of the output voltage of generator can be specifically influenced and the other one of the two half waves can be left largely uninfluenced. If switchable branches comprising capacitors are connected in parallel to both transistors, both half waves of the output voltage of the generator can be influenced independently from one another. This arrange- (Continued)

ment allows the specific influence of half oscillations of a push-pull generator that is apart therefrom symmetric, whereby the application spectrum for supply of medical instruments with treatment current is enlarged.

11 Claims, 3 Drawing Sheets

(56) References Cited

U.S. PATENT DOCUMENTS

2016/0380592 A1* 12/2016 Rajendran ............ H03D 7/1441
    455/118
2020/0345406 A1* 11/2020 Kato .................. A61B 18/1206

FOREIGN PATENT DOCUMENTS

| | | | |
|---|---|---|---|
| DE | 102008039884 A1 | 3/2010 | |
| DE | 102015014638 A1 * | 5/2017 | ............. H02J 50/12 |
| EP | 0949886 B1 | 9/2002 | |
| EP | 2753259 B1 | 4/2020 | |

* cited by examiner

GENERATOR FOR SUPPLYING MEDICAL INSTRUMENTS

CROSS REFERENCE TO RELATED APPLICATION

This application claims the benefit of European Patent Application No. 21217016.1, filed Dec. 22, 2021, which is incorporated herein by reference in its entirety.

TECHNICAL FIELD

The invention refers to a generator for supply of electrosurgical instruments, particularly a generator with improved control of the output voltage provided by the generator.

BACKGROUND

Many electrosurgical instruments, such as electrical scalpels, electrosurgical forceps or coagulation instruments, are typically supplied with radio frequency alternating current. For avoiding neuromuscular stimulation, the frequency of this alternating voltage is typically above 100 kHz. The power of such generators is typically considerably over 1 W and can reach multiple 100 W.

A generator for production of such voltages is apparent from DE 10 2008 039 884 A1. This generator comprises at least one oscillating circuit, which is excited to oscillate by means of an active transistor circuit and from which energy is decoupled in a transformer-type manner for supply of the connected instrument.

A generator for concurrent supply of multiple instruments is, for example, apparent from DE 60 2004 009 293 T2. This generator comprises multiple oscillating circuits that are connected to a full bridge circuit.

DE 29 10 196 A discloses a push-pull oscillator having two transistors that operate in push-pull manner, between the collectors of which a parallel oscillating circuit is arranged. By means of a coil coupling with the oscillating circuit coil in a transformer-type manner voltage and current are decoupled for a surgical instrument.

It has turned out that the wave form of the current supplied from the generator to the instrument has remarkable impacts on the physiological effect to be achieved. For this reason the desire for a possibility of influencing the wave form of the output voltage and the output current of a generator for supply of an instrument exists.

SUMMARY

Therefrom one object of the present invention is derived to provide a generator with extended possibilities for influencing the current and voltage form.

This object is solved by means of a generator as described herein.

The generator according to the invention is based on a concept having two amplifiers between the outputs of which an inductor of a resonance circuit is arranged. Assigned to the inductor is at least one first capacitor, with which it forms an oscillating circuit, as well as a second capacitor for additional influence of the resonance frequency of the oscillating circuit. Preferably thereby at least the second capacitor is connected to ground inseparably or via a switch, preferably an electronic switch. If the amplifier is realized by means of an electronic amplifying component, such as a bipolar transistor or a field effect transistor, one electrode of this capacitor is connected with the output electrode of the respective transistor (collector or drain) and the other electrode of the capacitor is connected to ground. In so far, the respective frequency influencing capacitor is switched in parallel to the amplifying component on the output side. Particularly, if the amplifying component operates in switching operation, it produces a temporary short circuit of the respective capacitor that therefore is temporarily ineffective. The capacitor influences only that half wave of the oscillation initiated at the oscillating circuit during which the amplifying component, to which it is connected in parallel, is non-conductive (high ohmic).

The generator is configured as push-pull oscillator. The two amplifiers are connected to a control circuit that is configured to control the amplifiers in a push-pull mode. Preferably the control circuit is configured to control the amplifiers in switching operation. This means the respective amplifying components (transistors) are either conductive for current, i.e. low ohmic conductive, or blocked.

The circuit concept according to the invention provides the specific influence on amplitude and duration of an individual half wave of such a generator. In doing so, specifically the positive (or also the negative) half waves of the generator oscillation can be enlarged or reduced in their amplitude as well as extended or shortened in time, for example. If multiple of such additional capacitors are connected with respective switches to the oscillating circuit and the associated amplifier output, the emerging generator oscillation can be influenced diversely so that also output wave forms of the voltage provided by the generator or the current provided by the generator can be created that cannot be created otherwise. For example, the oscillation provided to the instrument can be specifically created asymmetrically, e.g. to support or impede the spark formation at an instrument electrode.

As mentioned, the two amplifiers can be realized by electronic switches that are preferably controlled in a push-pull mode by means of a control circuit. The inductor can have a center tap via which operating current is supplied to the generator and thus the amplifiers. According to this concept, the generator is a symmetrical push-pull oscillator that can be brought in asymmetry condition by connecting and disconnecting of capacitors. Also an asymmetric supply is possible, particularly a high frequency high ohmic asymmetric supply.

BRIEF DESCRIPTION OF THE DRAWINGS

Details of circuit variants according to the invention are subject matter of dependent claims as well as the drawings and the respective description of its figures. The drawings show:

DETAILED DESCRIPTION

Figure 1:
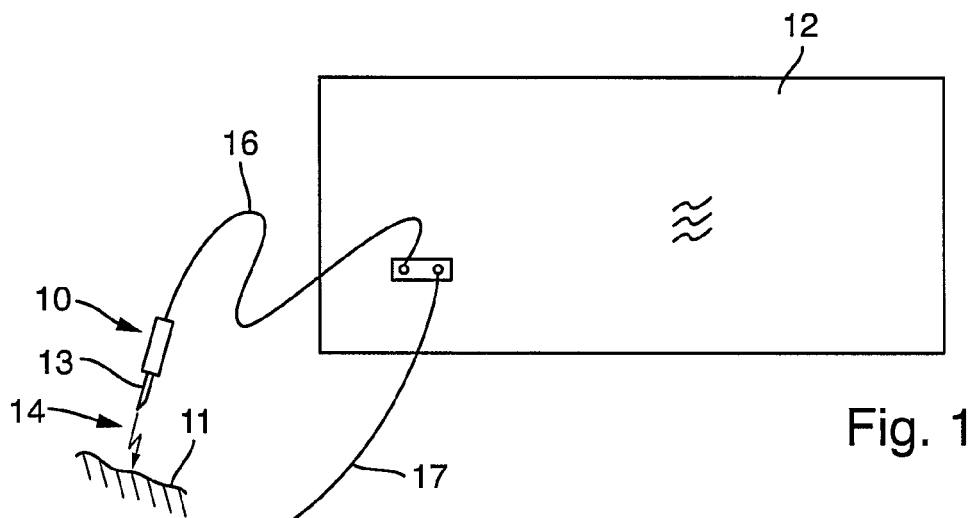
FIG. 1 a generator and a connected instrument in schematic overview illustration, FIG. 2 a generator for supply of the instrument in schematic circuit diagram illustration, FIG. 3 the output voltage of the generator according to FIG. 2 as schematic diagram, FIGS. 4-7 modified embodiments of the generator in principle circuit diagram respectively.

In FIG. 1 an instrument 10 for treatment of biological tissue 11 as well as a generator 12 for supply of the instrument 10 are illustrated. In the example a monopolar instrument 10 having one single electrode 13 is illustrated that influences on the biological tissue 11 by means of a spark 14. For guiding the current originating from the instrument 10 or the electrode 13 back to the generator 12 a neutral electrode 15 is provided that is to be attached to the human or animal patient of which the tissue 11 is a part. Lines 16, 17 connect the instrument 10 and the preferably large sized neutral electrode 15 with the generator 12. This arrangement is only an example. The generator 12 is also suitable for supply of bipolar instruments, such as for supply of coagulation tools having two or more electrodes. This applies particularly, because the generator 12 is in particular manner suitable to supply an output voltage Ua having a wave form that can be adapted to different physiological conditions and surgical requirements and tasks.

Figure 2:
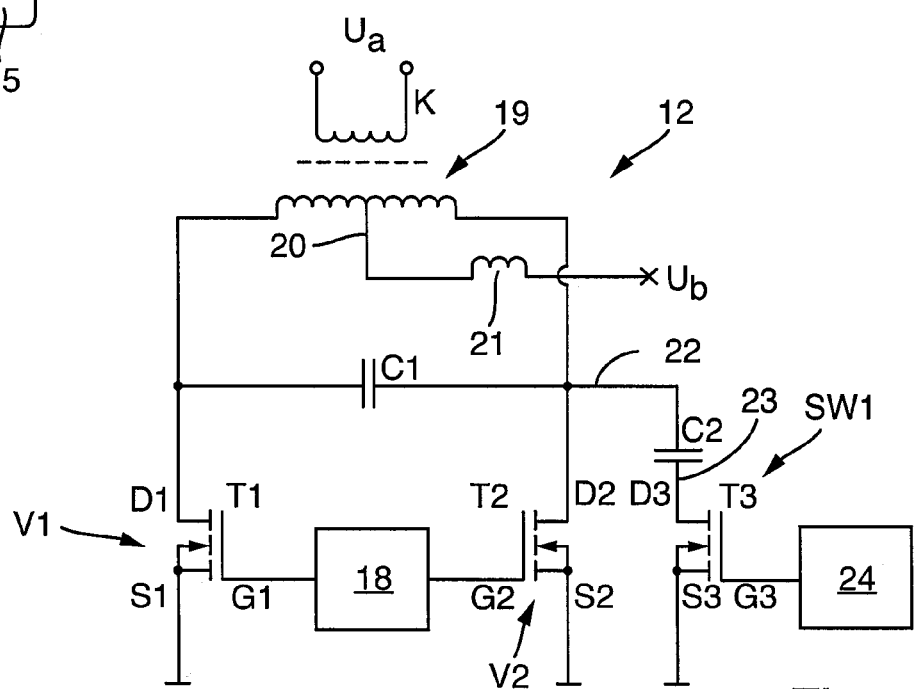

FIG. 2 illustrates the principal circuit of generator 12. It comprises a first amplifier V1 and a second amplifier V2 that can be realized by transistors T1, T2. The transistors T1, T2 are preferably field effect transistors, such as n-MOS-transistors of the enhancement type or depletion type. Other transistors, particularly bipolar transistors, IGBTs (bipolar transistors having an insulated gate) and the like can also be used. If the transistors T1 and T2 are field effect transistors, they respectively comprise a gate G1, G2, a source electrode S1, S2 as well as a drain electrode D1, D2. The two transistors T1, T2 operate in common source circuit so that the gates G1, G2 are the input electrodes of the amplifiers V1, V2. The drain electrodes D1, D2 are then the output electrodes of the amplifiers V1, V2.

The gates G1, G2 are connected with a control circuit 18 that is configured to open and close the transistors T1, T2 in an inversed manner, i.e. to make them conductive and non-conductive, according to a clock having the frequency of the alternating voltage to be created. The transistors T1, T2 are therefore controlled in push-pull mode and operate in switching operation. In all embodiments of generator 12 the control circuit 18 can be realized by two coupling capacitors, as exemplarily illustrated in FIG. 4, via which respectively one gate of one of the transistors is connected with the drain of the respective other transistor. This kind of coupling has the effect that always one of the transistors T1, T2 is conductive, while the respective other one of the two transistors T1, T2 blocks. The blocking and conducting phases change with the frequency predefined by the oscillating circuit. The two coupling capacitors are preferably dimensioned equally.

The source electrodes S1, S2 of the two amplifiers V1, V2 (transistors T1, T2) are connected to ground directly or at least with regard to alternating current. The output electrodes of the two amplifiers V1, V2, i.e. the drains D1, D2 of transistors T1, T2, are connected with one another by an inductor 19 that at least preferably comprises a center tap 20 via which the inductor 19 and therefore also the amplifiers V1, V2 are supplied with operating voltage Ub and therefore also with a respective operating current. In the supply line to the center tap 20 a choke 21 and as an option additional filter means can be provided. The choke 21 blocks a flow of high frequency current to the operating voltage source and in this manner avoids an undesired damping of the oscillation of the inductor.

The generator 12 comprises in addition a first capacitor C1 connected in parallel to inductor 19 in order to form a parallel oscillating circuit therewith. In this manner the first capacitor C1 connects the output electrodes of amplifiers V1 and V2, i.e. the drains D1 and D2, with each other.

The generator 12 described so far is in general able to oscillate and operable in the configuration described so far. However, it comprises additional means for influencing its operation. A second capacitor C2 is part thereof that is connected with one end to the parallel oscillating circuit formed by inductor 16 and capacitor C1 and is connected to ground with another end 23 inseparably or, as illustrated in FIG. 2, via a first switch SW1.

The first switch SW1 can be an electronic switch, e.g. in form of a transistor T3, which can be configured as field effect transistor, for example. It can be of the same type as transistors T1, T2 or also of another type. Its gate electrode G3 is connected to a control circuit 24 that opens or closes switch SW1 specifically for at least one oscillating period or also for a longer time interval.

The generator 12 described so far operates as follows:

The lines 16, 17 are connected with the voltage Ua produced by generator 12 in that lines 16, 17 lead to a coupling coil K that is inductively connected with inductor 19. The parallel oscillating circuit formed by inductor 19 and capacitor C1 is excited to oscillate in that the two amplifiers V1, V2 are operated in push-pull mode. For this transistors T1, T2 are alternatingly conductive and non-conductive. This is controlled by control circuit 18. The frequency and control of transistors T1, T2 preferably corresponds to the resonance frequency of the parallel oscillating circuit (inductor 19 and capacitor C1).

It is first assumed that switch SW1 is non-conductive, i.e. transistor T3 is blocked. Thereby the effective part of the circuit of generator 12 is configured symmetrically, capacitor C2 is non-effective. A symmetric oscillation is created as illustrated in the diagram in FIG. 3 during time period A.

The produced symmetric output voltage Ua is first provided as non-modulated output voltage. As necessary an amplitude modulation can be carried out, e.g. by means of modulating the operating voltage Ub. For the subsequent considerations it is, however, assumed that the operating voltage Ub is constant.

The output voltage Ua has during time period A a specific physiological effect, if the instrument 10 supplied therewith influences on the tissue 11, e.g. a coagulation effect. It is now assumed that another physiological effect is desired and generator 12 shall therefore produce an output voltage Ua having another wave form. Particularly, it shall have different oscillating progresses during the positive and the negative half wave, for example. For example, the half waves can distinguish in time duration and height (amplitude). For this purpose control circuit 24 closes switch SW1, i.e. it makes transistor T3 conductive between its source electrode S3 and its drain electrode D3. In this manner the end 23 of capacitor C2 is connected to ground. This electrical connection is maintained over the entire time period B illustrated in FIG. 3.

The second capacitor C2 is ineffective during the half wave in which transistor T2 is conductive. However, during the half wave in which T1 is conductive and transistor T2 is non-conductive, capacitor C2 is effective and connects the connection point between the first capacitor C1 and the inductor 19 to ground. Thereby a half wave can be created modified in amplitude and frequency, e.g. a smaller, but longer half wave. This oscillation of generator 12 can then have the form illustrated in FIG. 3 during time period B, for example. If the positive half wave is connected with the electrode 13 via line 16, the spark creation between electrode 13 and the biological tissue 11 is thereby supported and thus a different physiological effect is obtained than in time period A.

Figure 4:
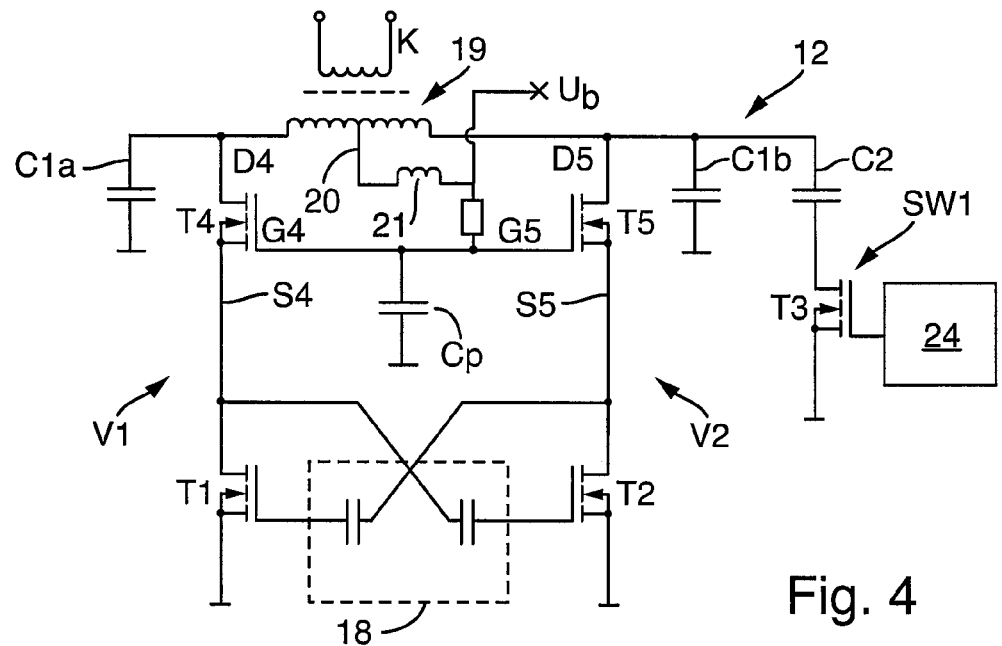

FIG. 4 illustrates a modified embodiment of generator 12 that only distinguishes from the embodiment described above in that the amplifiers V1, V2 are realized by cascode circuits from transistors T1, T2, T4, T5. The transistors T1, T2 correspond to the transistors T1, T2 according to FIG. 2. The transistors T4, T5 are connected in common gate circuit and thus form power amplifiers with their source electrodes S4, S5 as input electrodes, whereas their gate electrodes G4, G5 are connected to a suitable non-varying potential that is connected to ground via a capacitor Cp with regard to alternating currents.

Capacitor C1 is here divided into two individual capacitors C1a, C1b that are respectively connected to ground with one end. The respective other end of each capacitor C1a, C1b is connected with both ends of inductor 19. Again capacitors C1a, C1b form together with inductor 19 a parallel oscillating circuit. The switch SW1 serves for modification of the operation of generator 12 according to the circuit described in relation with FIG. 2. Particularly, it can make the oscillation of generator 12 asymmetric so that the latter can be switched between the oscillating form of time period A according to FIG. 3 and time period B according to FIG. 3 as required.

Figure 5:
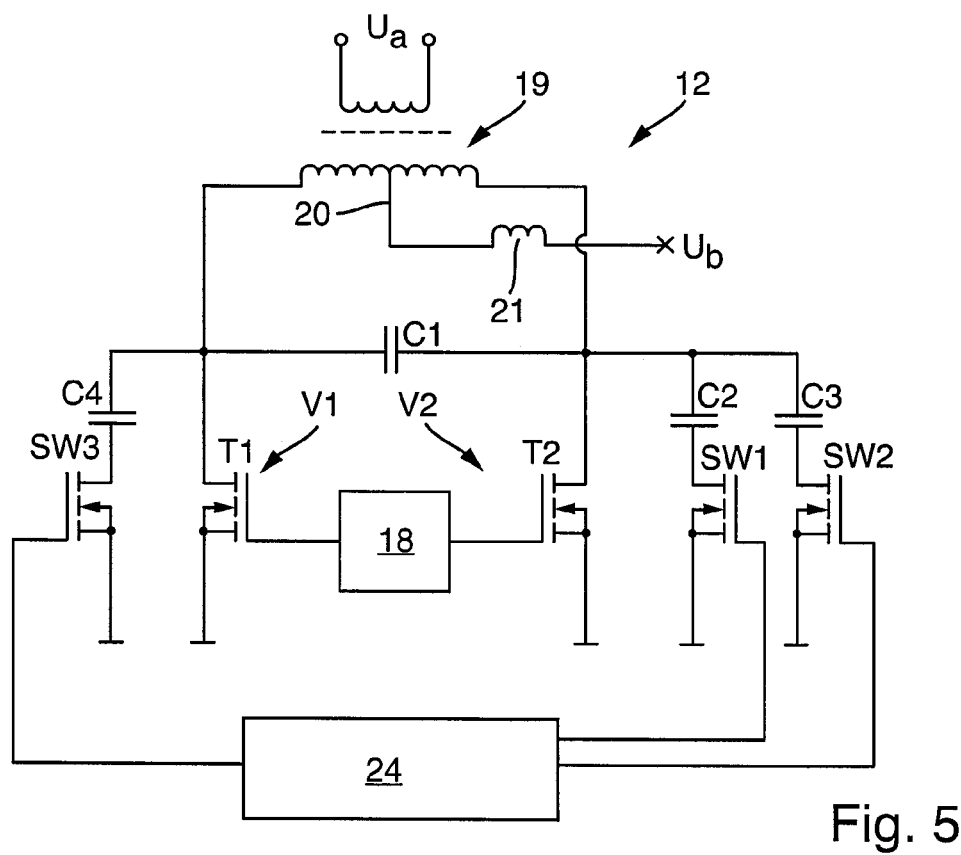

Independent from whether generator 12 is a simple push-pull generator according to the concept of FIG. 2 or a push-pull generator having amplifiers V1, V2 in cascode circuit according to FIG. 4, it can have in addition to the switch SW1 additional switches SW2, SW3 with capacitors C3, C4 in order to specifically influence the oscillation form of output voltage Ua. Such an example is shown in FIG. 5. Circuit branches are connected in parallel to both transistors T1, T2 and therefore both amplifiers V1, V2 in which circuit branches capacitors C2, C3, C4 are arranged in series connection with one switch SW1, SW2, SW3 to ground respectively. The control circuit 24 controls switches SW1, SW2, SW3 in order to connect one or multiple of capacitors or more of capacitors C2, C3, C4 to ground and in doing so to make the latter effective.

Similarly control circuit 24 can open one or more of switches SW1, SW2, SW3 (make it non-conductive) in order to thereby make one or more of capacitors C2, C3, C4 ineffective. If all capacitors C2, C3, C4 are ineffective, generator 12 oscillates according to the sample of time period A in FIG. 3. If one or more of capacitors C2, C3, C4 are activated in that the respective associated switch SW1, SW2, SW3 is closed (made conductive), the form of the output voltage Ua is deformed in characteristic manner, e.g. in that the positive or negative half wave is enlarged or reduced in its amplitude and shortened or extended in time.

Figure 6:
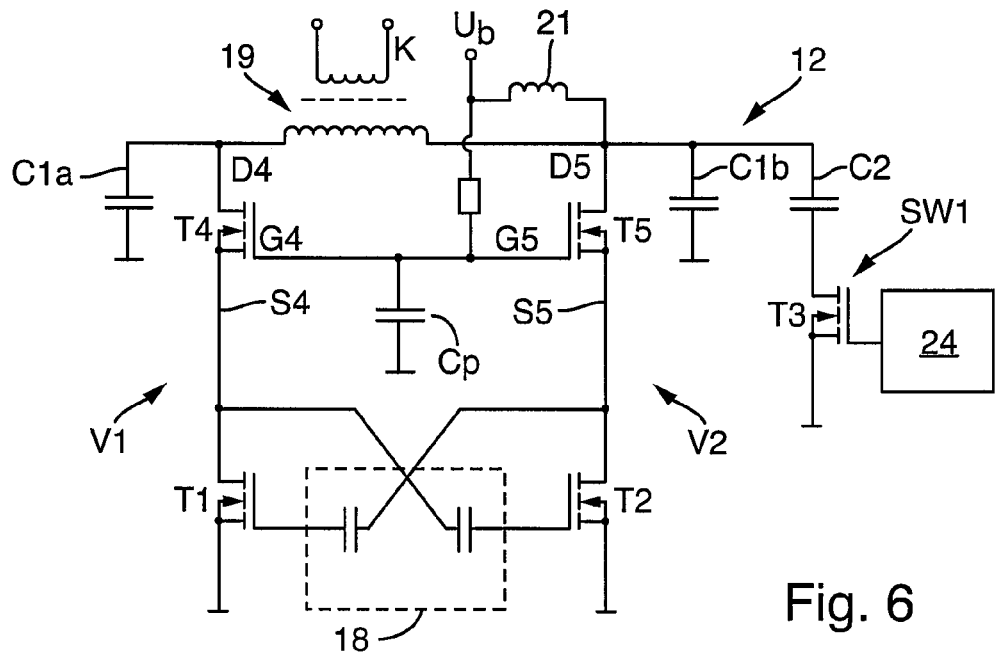
Figure 7:
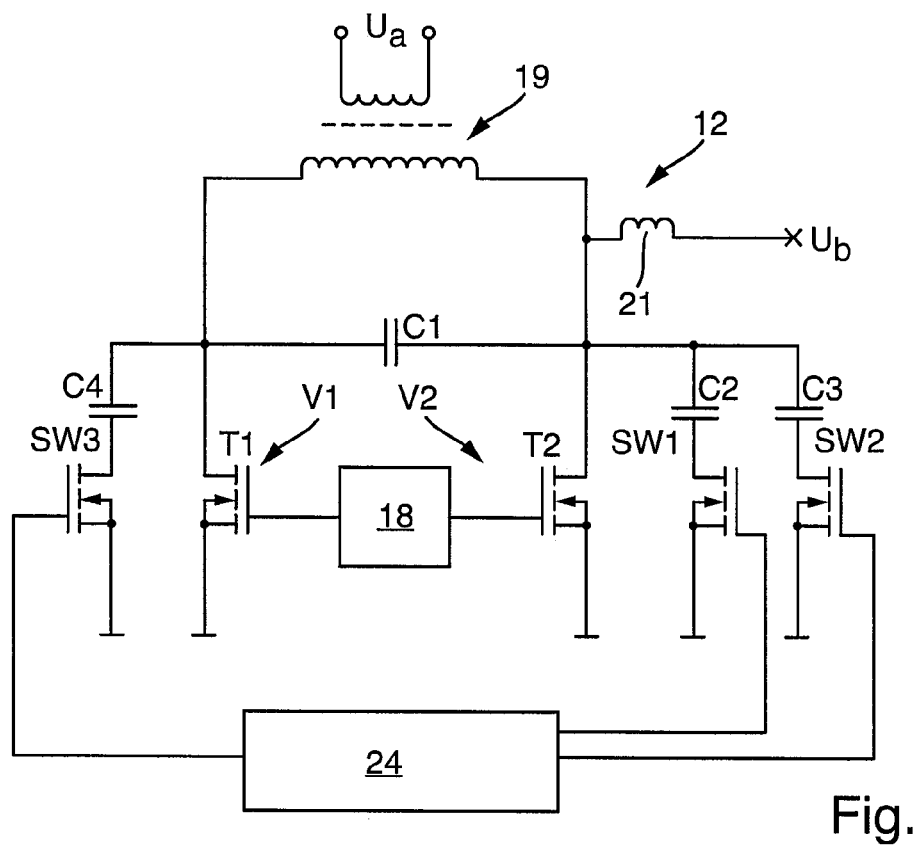

In all described embodiments one single switch SW1 together with capacitor C2 (FIGS. 2, 6), two switches SW1, SW2 with two capacitors C2, C3, three switches SW1, SW2, SW3 with three capacitors C2, C3, C4 (FIGS. 5, 7) or also multiple of such branches can be provided.

In the circuit concepts according to FIGS. 2-5 described above, the inductor 19 comprises a center tap 20 respectively to which operating current is supplied via a choke 21 that is high ohmic in relation to RF. In doing so, a symmetric current supply is provided. In all circuits mentioned above it is, however, also possible to asymmetrically supply the operating current via choke 21 at one end of inductor 19, as particularly apparent from FIGS. 6 and 7. Preferably the inductance of choke 21 is thereby higher than that of inductor 19. Because of the structure and the description of the function of these circuits according to FIGS. 6 and 7, reference is made to the description of the circuits according to FIGS. 4 and 5 on the basis of the already introduced reference signs. It applies in addition that due to the asymmetric supply of the operating current into generator 12 according to FIGS. 6 and 7, a start asymmetry is provided that may then also result in a not entirely symmetric oscillation, even if the additional capacitors C2, C3, C4 are ineffective, i.e. the associated switches SW1, SW2, SW3 are blocked. The present start asymmetry of the oscillation of generator 12 can be amplified or attenuated by specifically opening and closing one or multiple of the switches SW1, SW2, SW3.

A push-pull generator 12 provided for supply of a medical instrument 10 comprises at least one capacitive branch connected to ground, preferably in a switchable configuration, in parallel to at least one of its two transistors T1, T2. Such a capacitive switchable branch can consist of a series connection of one capacitor C2 and one switch SW1. Thereby one of the two half waves of the output voltage of generator 12 can be specifically influenced and the other one of the two half waves can be left largely uninfluenced. If switchable branches comprising capacitors C2, C4 are connected in parallel to both transistors T1, T2, both half waves of the output voltage Ua of generator 12 can be influenced independent from one another.

Therefore, the concept according to the invention allows the specific influence of half oscillations of a push-pull generator 12 that is apart therefrom symmetric, whereby the application spectrum for supply of medical instruments 10 with treatment current is enlarged.

Figure 3:
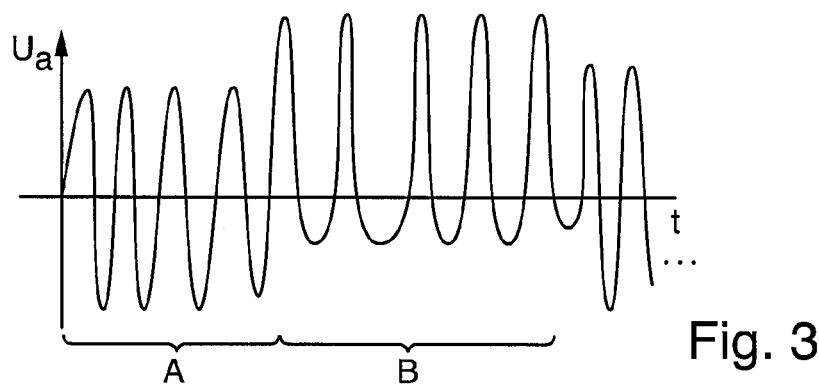

REFERENCE SIGNS 10 instrument
11 biological tissue
12 generator
13 electrode
14 spark
15 neutral electrode
16 line of instruments 10
17 line of neutral electrode 15
Ua voltage output from generator 12 to instrument 10
V1, V2 amplifier
T1-T5 transistors
G1-G5 gate electrodes
S1-S5 source electrodes
D1-D5 drain electrodes
18 control circuit
19 inductor
20 center tap
C1 first capacitor
C2 second capacitor
Cp buffer capacitor
21 choke
22 first end of capacitor C2
23 second end of capacitor C2
SW1 first switch
24 control circuit of switch SW1 (SW2, SW3)
K coupling coil
A, B time periods in FIG. 3
C4, C5 additional capacitors

The invention claimed is:
1. A system for treating a tissue of a patient, the system comprising:
 a surgical instrument (10) configured to treat the tissue (11) of the patient with at least one electrode (13) supplied with an electrical current; and
 a generator (12) for supply of the surgical instrument (10) with the electrical current comprising:
 a first amplifier (V1) that comprises a first input electrode (G1, S4) and a first output electrode (D1);

a second amplifier (V2) that comprises a second input electrode (G2, S5) and a second output electrode (D2);

an inductor (19) that is arranged between the first and the second output electrodes (D1, D2);

a first capacitor (C1) that is connected with the inductor (19) to form an oscillating circuit; and a second capacitor (C2) that comprises a first end (22) connected with the inductor (19) and a second end (23) connected with a switch (SW1);

a coupling coil (K) inductively connected with the inductor (19) for supplying the electrical current to the surgical instrument (10) via an electrical line (16); and a control circuit (24) configured to selectively open and close the switch (SW1) for generating a plurality of different wave forms of the electrical current, wherein the plurality of different wave forms of the electrical current have different physiological effects on the tissue of the patient when applied by the at least one electrode (13) of the surgical instrument (10);

wherein the first and second amplifiers (V1, V2) are connected with a push-pull control circuit (18).

2. The system according to claim 1, wherein the first amplifier (V1) is a first field effect transistor (T1), a drain electrode of which is the first output electrode (D1) and the second amplifier (V2) is a second field effect transistor (T2), a drain electrode of which is the second output electrode (D2).

3. The system according to claim 2, wherein the first input electrode (G1) is a gate electrode of the first field effect transistor (T1) and the second input electrode (G2) is a gate electrode of the second field effect transistor (T2).

4. The system according to claim 1, wherein the first amplifier (V1) is a first field effect transistor (T4), a drain electrode of which is the first output electrode (D4), the second amplifier (V2) is a second field effect transistor (T5), a drain electrode of which is the second output electrode (D5), the first input electrode (S4) is a source electrode of the first field effect transistor (T4) and the second input electrode (S5) is a source electrode of the second field effect transistor (T5).

5. The system according to claim 1, wherein the inductor (19) comprises a center tap (20) that is connected with an operating voltage source (Ub).

6. The system according to claim 1, wherein the inductor (19) is connected by one of its two ends with an operating voltage source (Ub).

7. The system according to claim 1, wherein the switch (SW1) is configured to selectively either terminate the second end (23) of the second capacitor (C2) in a high ohmic manner or to connect the second end (23) to ground.

8. The system according to claim 1, further comprising at least one additional capacitor (C3) that comprises a first end connected with the inductor (19) and a second end connected with a second switch (SW2), wherein the second switch (SW2) is configured to selectively either terminate the second end of the at least one additional capacitor (C3) in high ohmic manner or connect the second end to ground.

9. The system according to claim 1, wherein the first capacitor (C1) is connected in parallel with the inductor (19).

10. The system according to claim 1, wherein the first capacitor comprises two sub-capacitors (C1a, C1b) that respectively comprise one end connected to the inductor (19) and one end connected to ground.

11. The system according to claim 10, wherein the ends of the two sub-capacitors (C1a, C1b) connected to ground are respectively inseparably connected to ground.

* * * * *